United States Patent
Harris et al.

(10) Patent No.: US 9,265,640 B2
(45) Date of Patent: Feb. 23, 2016

(54) CONFORMING ANCHOR FOR DUODENAL BARRIER

(71) Applicant: Ethicon Endo-Surgery, Inc., Cincinnati, OH (US)

(72) Inventors: Jason L. Harris, Hamilton, OH (US); Mark S. Zeiner, Mason, OH (US); Adam R. Dunki-Jacobs, Cincinnati, OH (US); Justin W. Sherrill, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 223 days.

(21) Appl. No.: 14/011,987

(22) Filed: Aug. 28, 2013

(65) Prior Publication Data

US 2015/0065939 A1 Mar. 5, 2015

(51) Int. Cl.
*A61M 19/00* (2006.01)
*A61F 5/00* (2006.01)

(52) U.S. Cl.
CPC ............. *A61F 5/0076* (2013.01); *A61F 5/0079* (2013.01)

(58) Field of Classification Search
CPC ................ A61F 5/0079; A61F 5/0076; A61F 2002/045; A61M 27/002
USPC ............................................................ 604/8
See application file for complete search history.

(56) References Cited

U.S. PATENT DOCUMENTS

| | | | |
|---|---|---|---|
| 7,037,344 B2 | 5/2006 | Kagan et al. | |
| 7,121,283 B2 | 10/2006 | Stack et al. | |
| 7,267,694 B2 | 9/2007 | Levine et al. | |
| 7,931,693 B2 | 4/2011 | Binmoeller | |
| 8,043,248 B2 | 10/2011 | Pasricha | |
| 2005/0192614 A1* | 9/2005 | Binmoeller | 606/191 |
| 2008/0255678 A1 | 10/2008 | Cully et al. | |
| 2009/0187206 A1 | 7/2009 | Binmoeller et al. | |
| 2012/0221037 A1* | 8/2012 | Birk et al. | 606/191 |
| 2013/0030350 A1 | 1/2013 | Albrecht et al. | |
| 2013/0079603 A1 | 3/2013 | Vargas | |
| 2015/0065938 A1 | 3/2015 | Zeiner et al. | |

OTHER PUBLICATIONS

Non-Provisional U.S. Appl. No. US 14/011,962, filed Aug. 28, 2013.
International Search Report and Written Opinion dated Jan. 15, 2015 for Application No. PCT/US2014/052090.

* cited by examiner

*Primary Examiner* — Leslie Deak
(74) *Attorney, Agent, or Firm* — Frost Brown Todd LLC

(57) ABSTRACT

An apparatus comprises a sleeve, a seal, and an anchor assembly. The sleeve is flexible and non-permeable and is configured to fit in a duodenum. The seal is positioned at the proximal end of the sleeve and is configured to seal the proximal end of the sleeve against the stomach mucosa, the pylorus, or the duodenum mucosa. The anchor assembly comprises a pair of atraumatic anchor ends and a resilient member positioned between the anchor ends. At least a portion of the resilient member extends along at least a portion of the length of the sleeve. The resilient member is configured to bias the anchor ends generally toward each other, to thereby substantially anchor the sleeve in the duodenum. The sleeve is configured to prevent chyme from contacting the mucosa of the duodenum; and to prevent enzymes excreted in the duodenum from mixing with chyme in the duodenum.

18 Claims, 14 Drawing Sheets

US 9,265,640 B2

CONFORMING ANCHOR FOR DUODENAL BARRIER

BACKGROUND

In some instances, it may be desirable to deploy an endoluminal sleeve or other type of lining within a hollow body organ such as a stomach, intestine, etc. By way of example only, a sleeve may be positioned within a patient's duodenum to separate or bypass at least part of the food flow from the lined portions of the duodenum. In some patients, creating a physical barrier between ingested food and certain regions of the gastrointestinal wall by means of endoluminal sleeves may provide some degree of weight loss and/or treatment of type 2 diabetes. The presence of the barrier may influence or alter signaling (e.g., neural, endocrine, etc.) originating from the intestine and/or improve glycemic control. Contrary to traditional gastric bypass surgery, endoluminal sleeve surgery may be reversed and the sleeve may be removed after achievement of the desired clinical result.

An example of a duodenal sleeve is described in U.S. Pat. No. 7,267,694, entitled "Bariatric Sleeve," issued Sep. 11, 2007, the disclosure of which is incorporated by reference herein. The proximal end of a flexible, floppy sleeve of impermeable material defining a sleeve lumen is endoscopically deployed and anchored with the help of a barbed stent in the pylorus or in the superior section of the duodenum. The stent is also intended to ensure that the proximal lumen opening of the sleeve remains open. Chyme from the stomach enters the proximal lumen opening of the sleeve and passes through the sleeve lumen to the distal lumen opening. Digestive enzymes secreted in the duodenum pass through the duodenum on the outside of the sleeve, with the sleeve isolating the chyme from the enzymes. The enzymes and the chyme do not mix until the chyme exits from the distal lumen opening of the liner sleeve. In such a way, the efficiency of the process of digestion of the chyme may be diminished, reducing the ability of the gastrointestinal tract to absorb calories from the food. The sudden exposure of chyme to the small intestine (e.g., duodenum, proximal jejunenum, etc.) at the distal end of the barrier may lead to altered signaling from the gastrointestinal system resulting in an improved metabolic response.

Additional examples of endoluminal sleeves are disclosed in U.S. Pat. No. 7,121,283, entitled "Satiation Devices and Methods," issued Oct. 17, 2006, the disclosure of which is incorporated by reference herein; U.S. Pat. No. 7,037,344, entitled "Apparatus and Methods for Treatment of Morbid Obesity," issued May 2, 2006, the disclosure of which is incorporated by reference herein; U.S. Pub. No. 2008/0255678, entitled "Medical Apparatus and Method of Making the Same," published Oct. 16, 2008, the disclosure of which is incorporated by reference herein; and U.S. Pub. No. 2013/0030350, entitled "Devices and Methods for Anchoring an Endoluminal Sleeve in the GI Tract," published Jan. 31, 2013, the disclosure of which is incorporated by reference herein. Yet another example of an endoluminal sleeve is the EndoBarrier® by G.I. Dynamics, Inc. of Watertown, Mass.

It should be understood that an endoluminal sleeve positioned in the duodenum and/or elsewhere in the gastrointestinal tract may need to be substantially held in place to enable the sleeve to resist the driving forces of peristalsis in the gastrointestinal tract. The above-noted examples of endoluminal sleeves include various structures and techniques to substantially maintain the position of the sleeve in the gastrointestinal tract. U.S. Pat. No. 7,931,693, entitled "Method and Apparatus for Reducing Obesity," issued Apr. 26, 2011, the disclosure of which is incorporated by reference herein, discloses other structures and techniques that are used to substantially maintain the position of devices in the gastrointestinal tract. Similarly, U.S. Pub. No. 2009/0187206, entitled "Conformationally-Stabilized Intraluminal Device for Medical Applications," published Jul. 23, 2009, now U.S. Pat. No. 9,060,835, isssued Jun. 23, 2015, the disclosure of which is incorporated by reference herein, also discloses structures and techniques that may be used to substantially maintain the position of devices in the gastrointestinal tract.

While a variety of endoluminal sleeve devices and anchoring devices have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
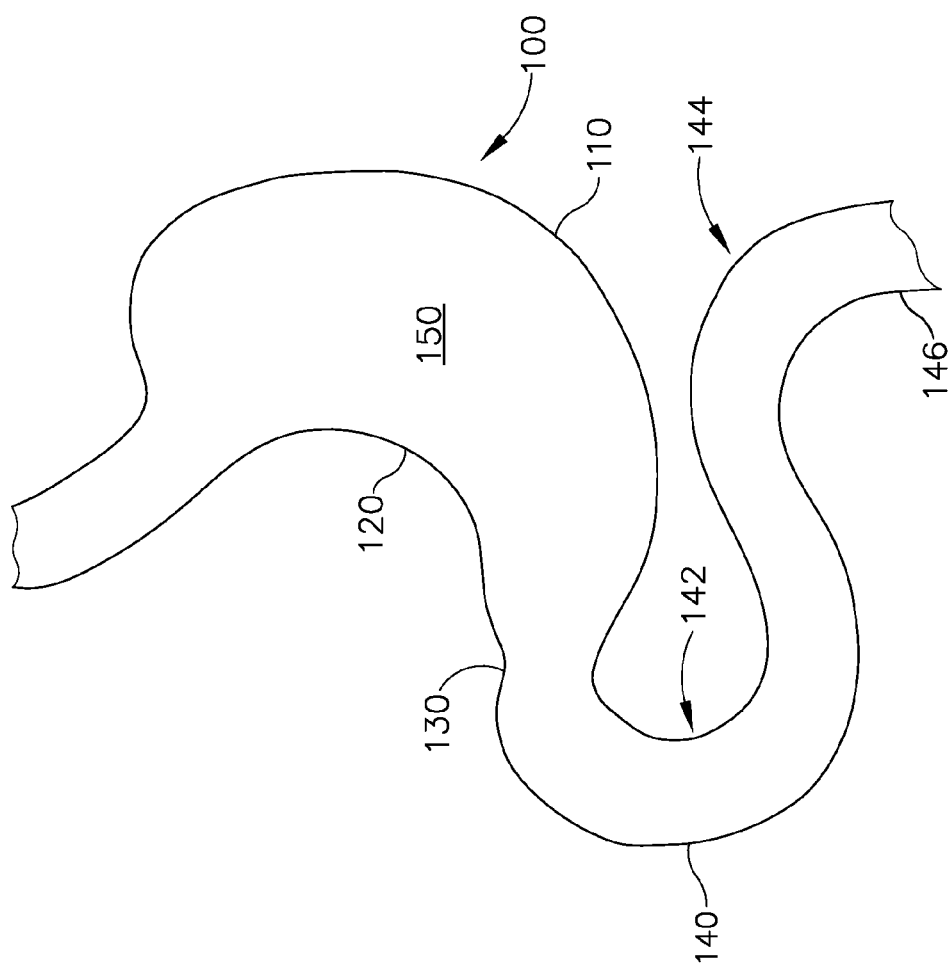
FIG. 1 depicts a side, diagrammatic view of an exemplary stomach and duodenum of a patient.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Duodenal Sleeve Assembly

FIG. 1 shows an exemplary stomach (100) and duodenum (140). It should be understood that stomach (100) and duodenum (140) may represent a stomach and duodenum of a patient with morbid obesity and/or type 2 diabetes. The stomach (100) comprises a hollow body (150) that includes the greater curvature (110) and the lesser curvature (120). The body (150) of the stomach (100) leads to the pylorus (130), which serves as a gateway from the stomach (100) to the duodenum (140). The duodenum (140) includes a region known as the ampulla of Vater (142). Further downstream, the duodenojejunal flexure (144) leads to the jejunum (146). The position of the duodenojejunal flexure (144) is associated with the location of the ligament of Treitz (not shown).

Figure 2A:
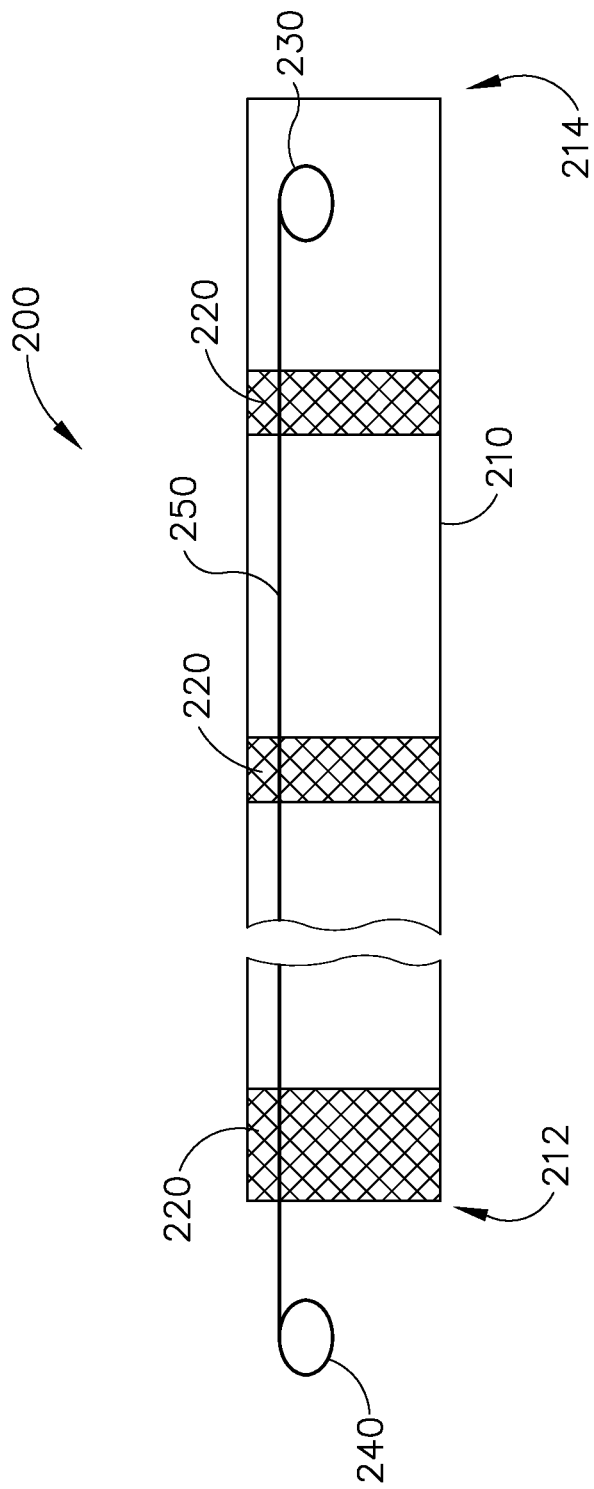
FIG. 2A depicts a side, elevation view of an exemplary duodenal sleeve assembly in a straight configuration.

FIG. 2A shows an exemplary duodenal sleeve assembly (200) for use in the stomach (100) and duodenum (140). A merely illustrative example of how sleeve assembly (200) may be deployed in the stomach (100) and duodenum (140) will be described in greater detail below. Sleeve assembly (200) of the present example comprises a flexible sleeve (210), a first anchor end (230), a second anchor end (240), and a resilient member (250) extending between anchor ends (230, 240). Duodenal sleeve assembly (200) further comprises resilient seals (220) that are integrated into flexible sleeve (210) to keep sleeve (210) open within the duodenum (140). In some versions, duodenal sleeve assembly (200) has just a single resilient seal (220). By way of example only, sleeve assembly (200) may have a single resilient seal (220) that is located at the proximal end of sleeve (210) when sleeve assembly (200) is in an implanted state. Thus, while several examples described herein include a plurality of seals in a single sleeve assembly, it should be understood that these are non-limiting examples. It is merely optional to include a plurality of seals in a single sleeve assembly.

Sleeve (210) of the present example comprises a flexible, non-permeable material that is configured to line at least part of the length of the duodenum (140). By way of example only, sleeve (210) may be constructed in accordance with at least some of the teachings of U.S. Pat. No. 7,267,694; U.S. Pat. No. 7,121,283; U.S. Pat. No. 7,037,344; U.S. Pub. No. 2008/0255678; and/or U.S. Pub. No. 2013/0030350, the disclosures of all of which are incorporated by reference herein. Sleeve (210) is dimensioned to complement the inner diameter of the duodenum (140). While the flexible material forming sleeve (210) is configured to fit the contours of duodenum (140), the material is also sufficiently durable such that sleeve (210) may withstand the forces of peristalsis in the duodenum (140). Furthermore, the material forming sleeve (210) is configured to withstand bile, enzymes in the duodenum (140), hydrochloric acid from the stomach (100), other chemicals/materials in the chyme passing from the stomach (100), etc.

When sleeve (210) lines the duodenum (140), sleeve (210) prevents the chyme that exits the stomach (100) from mixing with enzymes, etc. that are excreted in the duodenum (140) until the chyme exits the distal end (214) of sleeve (210). Sleeve (210) also prevents the duodenum (140) from absorbing fats or other nutrients from chyme along the length of sleeve (210). In some versions, sleeve (210) has a length selected such that sleeve (210) runs along at least the entire length of the duodenum (140). By way of example only, sleeve (210) may be configured such that distal end (214) is located at a region adjacent to the ligament of Treitz, at the duodenojejunal flexure (144), in the jejunum (146), or elsewhere when sleeve assembly (200) is deployed. In some other versions, sleeve (210) is shorter than the length of the duodenum (140). It should also be understood that sleeve (210) may be selectively permeable such that sleeve (210) allows the flow of certain substances across the barrier that is provided by sleeve (210).

Anchor ends (230, 240) and resilient member (250) cooperate to maintain the deployed positioning of sleeve (210) in the duodenum (140). Each anchor end (230, 240) has an atraumatic loop shape in the present example. Alternatively, each anchor end (230, 240) may have some other atraumatic shape such as a ball shape, a spoon shape, etc. By way of example only, anchor ends (230, 240) may be configured in accordance with at least some of the teachings of U.S. Pat. No. 7,931,693 and/or U.S. Pub. No. 2009/0187206, now U.S. Pat. No. 9,060,835, issued Jun. 23, 2015, the disclosures of which are incorporated by reference herein. In addition or in the alternative, either or both anchor end (230, 240) may include one or more barbs, ridges, protuberances, and/or other outwardly extending features. In some versions, the configurations of anchor ends (230, 240) permit transoral placement and removal of sleeve assembly (200). Various other suitable ways in which anchor ends (230, 240) may be configured will be apparent to those of ordinary skill in the art in view of the teachings herein.

In the present example, the atraumatic configuration of anchor ends (230, 240) permits the distal-most anchor end (230) to bear against the inner wall of the duodenum (140) during positioning of sleeve assembly (200), without the distal-most anchor end (230) rupturing sleeve (210) or snagging on the mucosa of the duodenum (140). Anchor ends (230, 240) may also be configured to provide sufficient friction such that when anchor ends (230, 240) are urged against the inner wall of the stomach (100) and duodenum (140), anchor ends (230, 240) provide a grip that maintains the deployed positioning of sleeve assembly (200). In addition or in the alternative, the complementary relationship between the geometry of the deployed resilient member (250) and the geometry of the duodenum (140) may maintain the deployed positioning of sleeve assembly (200). In other words, resilient member (250) and anchor ends (230, 240) need not necessarily act like a clamp bearing on tissue, with anchor ends (203, 240) exerting forces in substantially opposing directions, in order for to resilient member (250) and anchor ends (230, 240) to secure the position of the deployed sleeve assembly (200) in the duodenum (140).

Resilient member (250) joins anchor end (230) and anchor end (240). In the present example, resilient member (250) is in the form of a wire. However, it should be understood that resilient member (250) may comprise a bar, a beam, and/or any other suitable structure. By way of example only, resilient member (250) may have a cross-sectional profile that is circular, rectangular, elliptical, or any other suitable shape.

Resilient member (250) may be formed of a resilient metal (e.g., nitinol, etc.), a resilient plastic, and/or any other suitable kind of material or combination of materials. Resilient member (250) of the present example has a fixed length, though it should be understood that some other versions may provide variable length (e.g., via sliding/telescoping segments, elastic/plastic elongation, etc.).

Figure 2B:
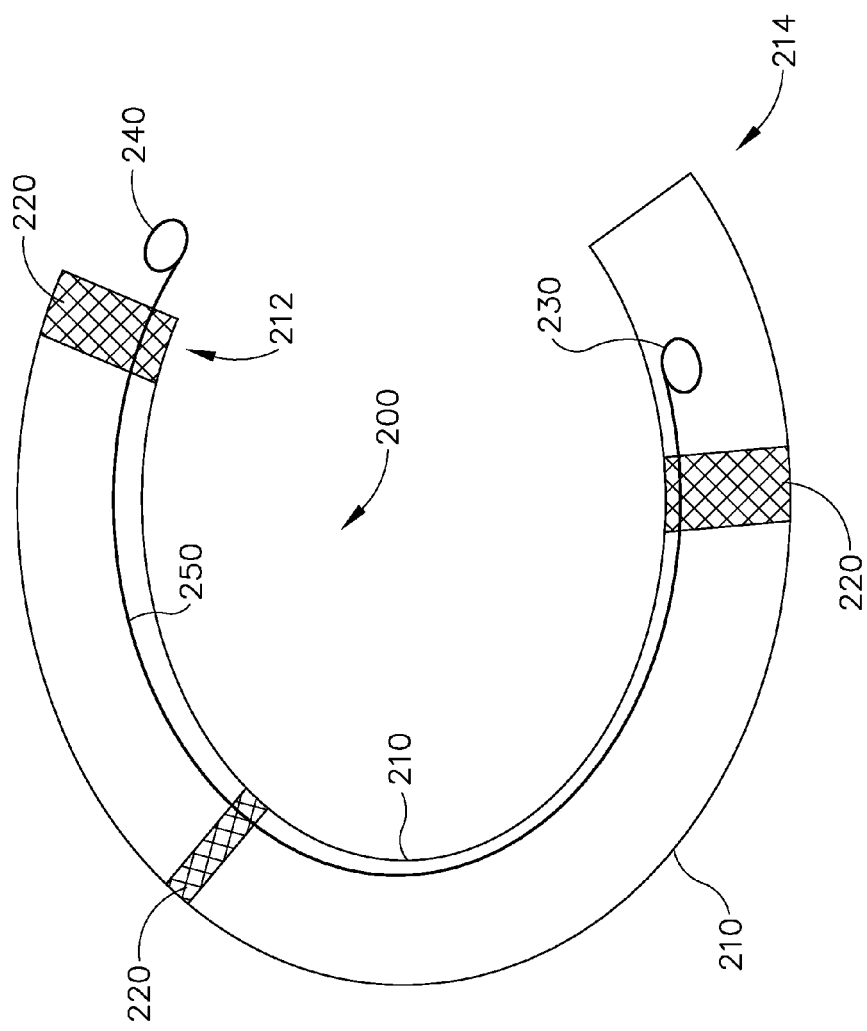
FIG. 2B depicts a side, elevation view of the sleeve assembly of FIG. 2A in a bent configuration.

FIG. 2A shows resilient member (250) in a straightened configuration while FIG. 2B shows resilient member (250) in a bent configuration, with resilient member (250) being positioned at the inner curvature of sleeve (210). In the present example, resilient member (250) is resiliently biased to assume the bent configuration in FIG. 2B. In particular, resilient member (250) is configured to resiliently bias anchor ends (230, 240) generally toward each other. In this example, the term "generally toward each other" is intended to indicate that anchor ends (230, 240) are biased by forces acting along paths that are substantially transverse to the localized longitudinal axis of resilient member (250), though these paths are not necessarily in exactly opposite directions. The term "generally toward each other" should thus be understood to mean that the resilient bias of resilient member (250) urges anchor ends (230, 240) away from a longitudinal axis defined by a straightened resilient member (250) as shown in FIG. 2A and toward positions such as those shown in FIG. 2B, where anchor ends (230, 240) are closer to each other than they otherwise would be with resilient member (250) in the straightened position shown in FIG. 2A.

Resilient member (250) is configured to transition from its natural configuration shown in FIG. 2B to a deployment configuration as shown in FIG. 2A with little or no plastic deformation of resilient member (250). Thus, once resilient member (250) is deployed within the gastrointestinal tract as will be described in greater detail below, resilient member (250) will generally return to (or at least toward) its natural configuration from the deployment configuration without other external interventions. In this way, anchor ends (230, 240) may be biased generally toward each other in the patient and maintain the system within the proximal duodenum (140). This region of the duodenum (140) is retro-peritoneal and is therefore relatively fixed in its geometry, unlike the remainder of the small intestine. In its natural configuration, resilient member (250) matches, approximates, or otherwise generally conforms to this fixed anatomical geometry, as alluded to above. Resilient member (250) is sufficiently stiff to not be dislodged from a deployed location in the duodenum (140). In particular, the stiffness of resilient member (250) opposes peristaltic and other physiological forces applied to it that seek to straighten or otherwise deform resilient member (250) into a configuration that can be passed further distally in the small intestine. In other words, the combination of stiffness and geometry of resilient member (250) in its natural configuration, in cooperation with the fixed geometry of the duodenum (140), maintain the position of the deployed resilient member (250) within the gastrointestinal tract (e.g., rather than a clamping action by anchor ends (230, 240)). Resilient member (250) is stiff enough to meet this aim while maintaining its resilience to deform between natural and deployment configurations as described herein. Various ways in which resilient member (250) may achieve this balance of stiffness and flexibility will be apparent to those of ordinary skill in the art in view of the teachings herein. It should also be understood that the natural configuration shown in FIG. 2A and the deployment configuration shown in FIG. 2B are merely illustrative examples. Other suitable natural configurations and/or deployment configurations may be used.

Resilient member (250) may be integrated into sleeve (210). For instance, resilient member (250) may be secured to the exterior of sleeve (210). In some other versions, resilient member (250) is secured to the interior of sleeve (210). In some other versions, sleeve (210) is formed by at least two apposed layers of material, and resilient member (250) is interposed between two such layers of material. In still other versions, resilient member (250) is not secured to sleeve (210), but instead just resiliently bears against sleeve (210) or anchor ends (230, 240) at one or more locations. As yet another merely illustrative example, resilient member (250) may be secured only to the proximal-most seal (220), such that resilient member (250) is not otherwise directly coupled to any portion of sleeve (210) that is distal to seal (220). Still other suitable relationships between resilient member (250) and sleeve (210) will be apparent to those of ordinary skill in the art in view of the teachings herein.

Resilient seals (220) are located at various positions along the length of sleeve (210). Resilient seals (220) are configured as resiliently expandable stents in the present example, though it should be understood that resilient seals (220) may have any suitable shape (e.g., annular, cylindraceous, etc.). By way of example only, resilient seals (220) may be in the form of expandable rings and/or cuffs that are coaxial with sleeve (210). In particular, resilient seals (220) may be resiliently biased to expand outwardly; yet may collapse to a reduced diameter to facilitate deployment of sleeve assembly (200). Seals (220) may be formed of plastic membrane encased nitinol and/or any other suitable material(s). In an outwardly expanded configuration, resilient seals (220) are configured to urge sleeve (210) radially outwardly and into contact with the mucosa of the duodenum (140). Resilient seals (220) thus assist in holding sleeve (210) in an open configuration. The proximal-most resilient seal (220) is configured to bear against the wall of the duodenum (140) just distal to the pylorus (130) and proximal to the ampulla of Vater (142), thereby sealing the proximal end (212) of sleeve (210) against the mucosa of the duodenum (140) and preventing chyme from reaching the mucosa of the duodenum (140) at the proximal end (212) of sleeve (210). In other words, the proximal-most resilient seal (220) directs chyme into the lumen defined by sleeve (210). In addition to assisting in keeping sleeve (210) open, seals (220) may also assist in securing the localized longitudinal position of sleeve (210) in the duodenum (140), thereby preventing sleeve (210) from bunching up within the duodenum (140), etc.

While three resilient seals (220) are shown, it should be understood that any other suitable number of resilient seals (220) may be used. By way of example only, some versions of sleeve assembly (200) have just one resilient seal (220), positioned at the proximal end (212) of sleeve (210). It should also be understood that different resilient seals (220) within the same sleeve assembly (200) may be configured differently. For instance, the proximal-most resilient seal (220) at the proximal end (212) of sleeve (210) may have a cylindraceous cuff shape while the other resilient seals (220) have shorter ring shapes. Other suitable configurations for resilient seals (220) will be apparent to those of ordinary skill in the art in view of the teachings herein.

By way of example only, resilient seals (220) may be secured to the exterior of sleeve (210). In some other versions, resilient seals (220) are secured to the interior of sleeve (210). In some other versions, sleeve (210) is formed by at least two apposed layers of material, and resilient seals (220) are interposed between two such layers of material. As yet another merely illustrative example, sleeve (210) may be coupled with the proximal-most seal (220) in accordance with at least some of the teachings of U.S. patent application Ser. No. 14/011,962, entitled "Endoscopic Transoral Duodenal Sleeve Applier," filed on Aug. 28, 2013, now U.S. Pat. Pub. No. 2015/0065938, published Mar. 5, 2015, the disclosure of which is incorporated by reference herein. Still other suitable relationships between resilient seals (220) and sleeve (210) will be apparent to those of ordinary skill in the art in view of the teachings herein. It should also be understood that resilient member (250) may be secured to one or more of seals (220), if desired.

Figure 3:
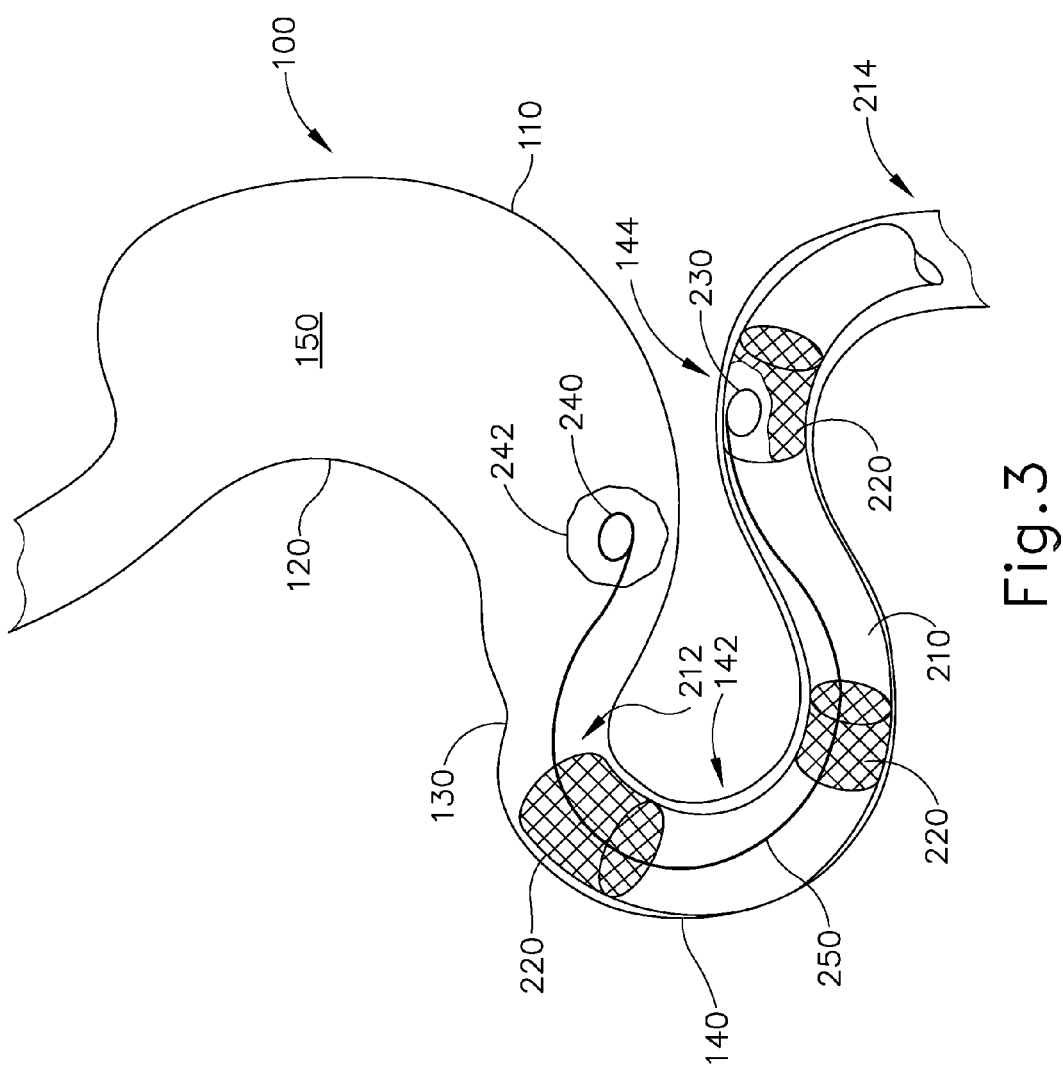
FIG. 3 depicts a side, elevation view of the sleeve assembly of FIG. 2A in the stomach and duodenum of FIG. 1.

FIG. 3 shows sleeve assembly (200) deployed in the stomach (100) and duodenum (140). In particular, sleeve assembly (200) is positioned such that the proximal end (212) of sleeve (210) and the associated seal (220) are located at the between the pylorus (130) and the ampulla of Vater (142), with the remainder of sleeve (210) extending along the rest of the length of the duodenum (140). Sleeve (210) lines the mucosa of the duodenum (140), thereby isolating chyme within sleeve (210) from enzymes, etc., excreted in the duodenum (140); and preventing the duodenum (140) from absorbing fat and other nutrients from chyme within sleeve (210). Resilient seals (220) bear outwardly against sleeve (210) and the duodenum (140), thereby holding sleeve (210) in an open configuration. The seal (220) at the proximal end (212) of sleeve (210) seals the proximal end (212) of sleeve (210) against the duodenum (140) just distal to pylorus (130), thereby ensuring that chyme exiting the stomach (100) directly enters sleeve (210) from the pylorus (130). In some other versions, the proximal end (212) of sleeve (210) and the associated seal (220) are positioned in the stomach (100), just proximal to (upstream of) the pylorus (130). In still other versions, the proximal-most seal (220) may be configured to longitudinally span at least part of the pylorus (130).

Continuing with the example shown in FIG. 3, the proximal anchor end (240) is positioned proximal to the proximal end (212) of sleeve (210), within the body (150) of the stomach (100). Proximal anchor end (240) is located near the pyloric part of the stomach (100). In some versions, proximal anchor end (240) is located at the pyloric antrum of the stomach (100). In some other versions, proximal anchor end (240) is located elsewhere along the greater curvature (110) of the stomach (110). Other suitable positions for proximal anchor end (240) will be apparent to those of ordinary skill in the art in view of the teachings herein. The resilient bias of resilient member (250) urges proximal anchor end (240) downwardly toward the distal anchor end (230), such that proximal anchor end (240) applies pressure (sufficient for fixation without causing erosions or other negative effects) to the wall of the stomach (100) in the direction of the shortest distance between anchor ends (230, 240).

In the example shown in FIG. 3, proximal anchor end (240) is enclosed by a bladder (242). Bladder (242) may comprise an inflatable bladder containing saline, gel, and/or any other suitable material. Bladder (242) may include a port that allows bladder (242) to be selectively filled or emptied once bladder (242) has been positioned in the stomach (100). Bladder (242) may soften the contact between anchor end (240) and the mucosa of the stomach (100), distributing the pressure of anchor end (240) against a greater surface area than would otherwise be provided by anchor end (240) alone. Bladder (242) is sized such that, when bladder (242) is filled or otherwise expanded, bladder (242) does not advance through pylorus (130). In some versions, bladder (242) may be weighted such that bladder (242) is operable to secure and/or urge anchor end (240) toward greater curvature (110), thereby further securing anchor end (240) within stomach (100), while still allowing chyme to pass through pylorus (130) for digestion. In other versions, it will be appreciated that a combination of the mass of bladder (242) along with the resilient bias of member (250) is operable to secure sleeve assembly (200). Of course, bladder (242) is merely optional. For instance, proximal anchor end (240) may instead contact the inner wall of stomach (100) directly.

It should also be understood that distal anchor end (230) may include a fillable bladder that is similar to bladder (242). In addition or in the alternative, resilient member (250) may include one or more fillable bladders. For instance, a single fillable bladder may extend along all or part of the length of resilient member (250). Alternatively, a plurality of fillable bladders may be spaced along at least part of the length of resilient member (250). Other suitable bladder configurations will be apparent to those of ordinary skill in the art in view of the teachings herein. As noted above, a filled bladder (or other form of cushioning) may soften the contact between anchor end (230) and the mucosa of the duodenum (140) and/or between resilient member (250) and the mucosa of the duodenum (140), distributing the pressure of anchor end (230) and/or resilient member (250) against a greater surface area than would otherwise be provided by anchor end (230) and/or resilient member (230) alone.

As shown in FIG. 3, distal anchor end (230) is positioned within sleeve (210) at a resilient seal (220) located at the duodenojejunal flexure (144). It should be understood, however, that a resilient seal (220) need not necessarily be positioned at the location where distal anchor end (230) bears against sleeve (210). The distal end (214) of sleeve (210) is distal to distal anchor end (230) in this example, though such an arrangement is merely optional. For instance, anchor end (230) could be positioned distal to the distal end (214) of sleeve (210). While distal anchor end (230) is positioned at the duodenojejunal flexure (144) in the present example, distal anchor end (230) may instead be positioned elsewhere within the duodenum (140) or even within the jejunum (146). While a bladder (242) is not shown on anchor end (230) in this example, it should be understood that anchor end (230) may include a bladder (242) and/or some other feature, in addition to or in lieu of anchor end (240) having a bladder (242), etc.

The resilient bias of resilient member (250) urges distal anchor end (230) upwardly toward the proximal anchor end (240), such that distal anchor end (230) applies pressure to the wall of the duodenum (140) in the direction of the shortest distance between anchor ends (230, 240). In other words, anchor ends (230, 240) are resiliently biased toward each other. Anchor ends (230, 240) and resilient member (250) thus cooperate to maintain the position of sleeve assembly (200) as shown in FIG. 3, even during peristalsis of the stomach (100) and duodenum (140). It should be understood that some versions may resiliently apply pressure to tissue at anchor ends (230, 240) only; while other versions may also resiliently apply pressure to tissue along at least part of the length of resilient member (250). In still other versions, seals (220) may be configured to provide a set-off between resilient member (250) and the mucosa of the duodenum (140), such that resilient member (250) is centrally located within sleeve (210) or is otherwise interiorly spaced away from the mucosa of the duodenum (140). As yet another variation, the distal-most seal (220) may act as a set-off between distal anchor end (240) and the mucosa of the duodenum (140), such that distal anchor end (240) is centrally located within sleeve (210) or is otherwise interiorly spaced away from the mucosa of the duodenum (140). Other suitable arrangements will be apparent to those of ordinary skill in the art in view of the teachings herein.

Figure 4:
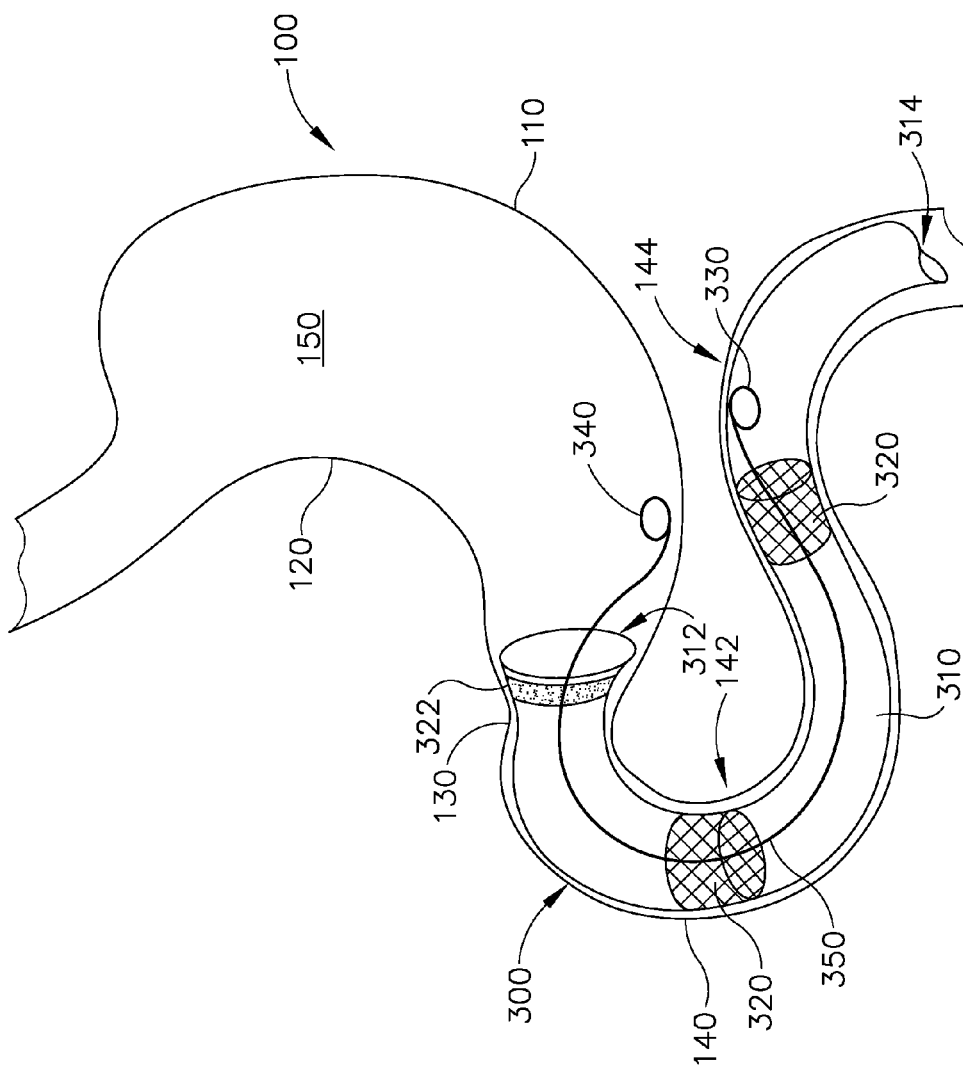
FIG. 4 depicts a side, elevation view of an exemplary alternative sleeve assembly for use in the stomach and duodenum of FIG. 1.

FIG. 4 shows an exemplary alternative sleeve assembly (300), which is an illustrative variation of sleeve assembly (200). Sleeve assembly (300) of this example comprises a flexible sleeve (310), a pair of anchor ends (330, 340), resilient member (350) extending between anchor ends (330, 340), and resilient seals (320). Sleeve (310) of this example is substantially identical to sleeve (210) described above; and includes a proximal end (312) and a distal end (314). Anchor ends (330, 340) and resilient member (350) are substantially identical to anchor ends (230, 240) and resilient member (250), respectively, described above. Resilient seals (320) are also identical to resilient seals (220) described above. However, sleeve assembly (300) of this example includes a sealing ring (322) that is located in sleeve assembly (300) where the proximal-most seal (220) was located in sleeve assembly (200). Sealing ring (322) is secured near the proximal end (312) of sleeve (310). In the present example, sealing ring (322) is resiliently biased to an expanded configuration where sealing ring (322) has a diameter that is greater than the diameter of the opening defined by the pylorus (130). Thus, when sealing ring (322) is in an expanded state, sealing ring (322) is configured to not pass through the pylorus (130). In some versions, sealing ring (322) is rigid or semi-rigid, such that sealing ring (322) is substantially inflexible. In some other versions, sealing ring (322) comprises a resilient member (e.g., plastic coated nitinol) that is secured to sleeve (310) and/or resilient member (350). As yet another variation, sealing ring (322) may be defined by a bent portion of resilient member (350). It should therefore be understood that sealing ring (322) need not necessarily form a complete circle, but may instead form a substantially complete circle (i.e., complete enough to provide an effective seal against the mucosa of the stomach (100)).

As shown in FIG. 4, sealing ring (322) may be positioned within the stomach (100), substantially coaxial with the pylorus (130) and just proximal to the pylorus (130), when sleeve assembly (300) is deployed. Sealing ring (322) holds the proximal end (312) of sleeve (310) against the mucosa of the stomach (100), thereby sealing the proximal end (312) of sleeve (310) against the mucosa of the stomach (100). Sealing ring (322) thus holds the proximal end of sleeve (312) open and ensures that chyme leaves the stomach (100) through sleeve (310) rather than exiting through the pylorus (130) and contacting the mucosa of the duodenum (140) and immediately mixing with enzymes, etc. excreted in the duodenum (140). Anchor ends (330, 340) and resilient member (350) cooperate to maintain the position of sleeve (310) in the duodenum (140). It should therefore be understood that sleeve assembly (300) may operate substantially identically to sleeve assembly (200), with the primary difference being that the proximal end (312) of sleeve (310) and its associated sealing feature are positioned in the stomach (100) instead of being positioned in the duodenum (140) like the proximal end (212) and the associated sealing feature of sleeve (210). It should also be understood that sealing ring (322) may also assist in securing the position of sleeve (310) in the duodenum (140), in addition to providing a seal at the proximal end (312) of sleeve (310).

Figure 5:
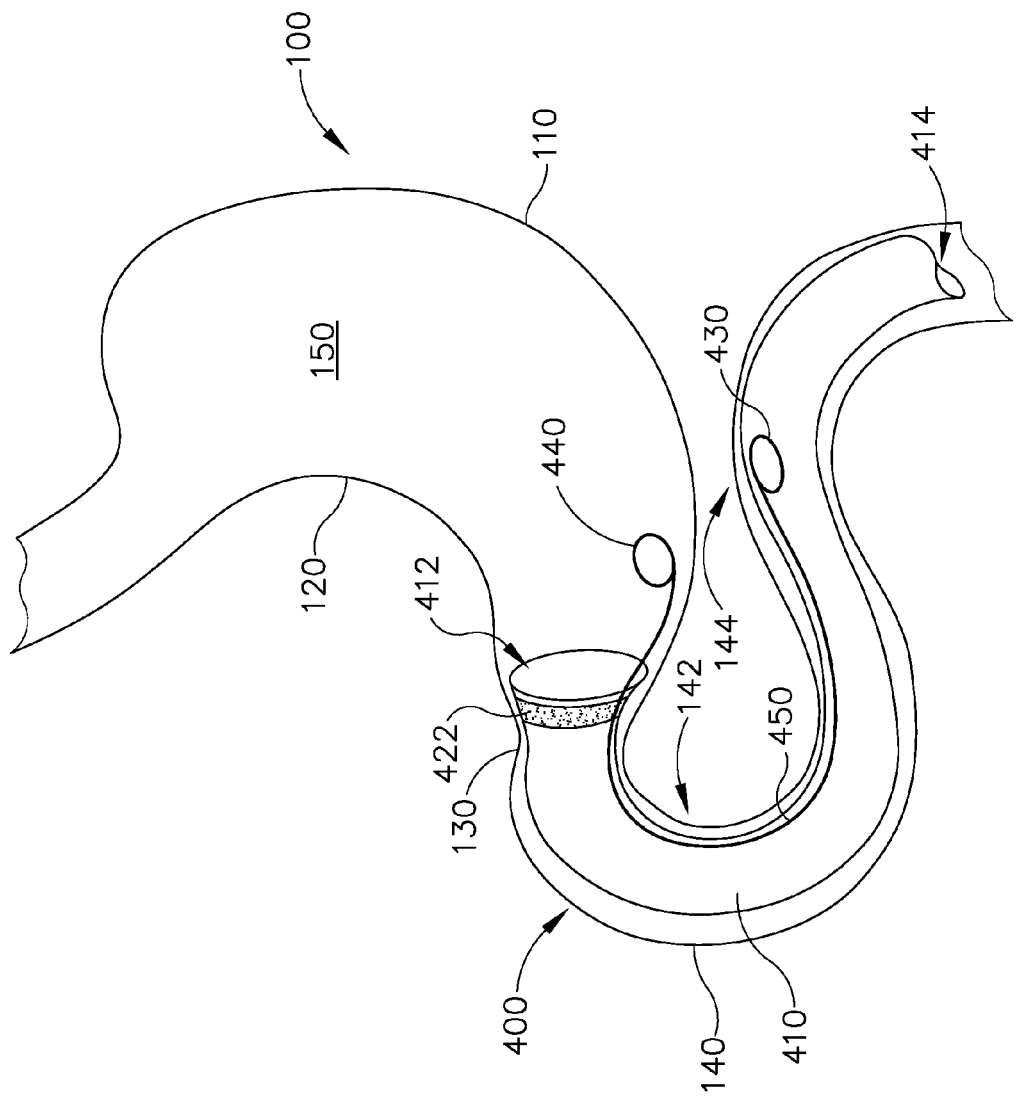
FIG. 5 depicts a side, elevation view of yet another exemplary alternative sleeve assembly for use in the stomach and duodenum of FIG. 1.

FIG. 5 shows another exemplary alternative sleeve assembly (400), which is an illustrative variation of sleeve assembly (200). Sleeve assembly (400) of this example comprises a flexible sleeve (410), a pair of anchor ends (430, 440), resilient member (450) extending between anchor ends (430, 440), and a sealing ring (422). Sleeve (410) of this example is substantially identical to sleeve (210) described above; and includes a proximal end (412) and a distal end (414). Anchor ends (430, 440) and resilient member (450) are substantially identical to anchor ends (230, 240) and resilient member (250), respectively, described above. Sealing ring (422) is substantially identical to sealing ring (322) described above.

Unlike sleeve assemblies (200, 300) described above, sleeve assembly (400) of the example shown in FIG. 5 lacks seals (220, 320). Instead, sealing ring (422) is the only sealing member of sleeve assembly (400). It should be understood that resilient member (450) may also track along the inner curvature of the duodenum (140) more closely as shown in this example than the resilient member (250, 350) of sleeve assemblies (200, 300), such that resilient member (450) is not substantially set off from the mucosa of the duodenum (140). Despite the above-noted differences, sleeve assembly (400) may nevertheless function substantially identically to sleeve assemblies (200, 300) described above, with anchor ends (430, 440), resilient member (450) and sealing ring (422) all cooperating to maintain proper positioning of sleeve (410) in the duodenum (140).

Figure 6:
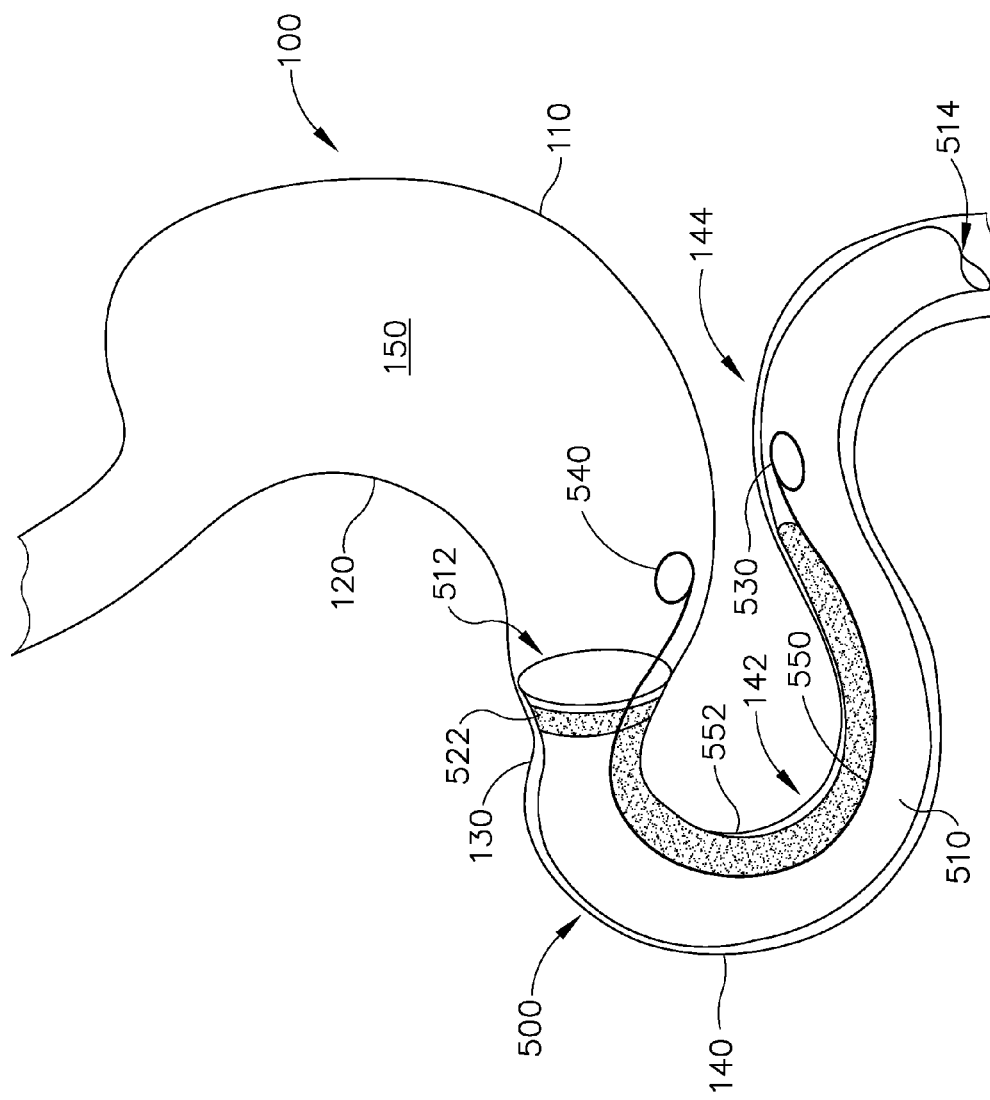
FIG. 6 depicts a side, elevation view of yet another exemplary alternative sleeve assembly for use in the stomach of FIG. 1.

FIG. 6 shows another exemplary alternative sleeve assembly (500), which is an illustrative variation of sleeve assembly (200). Sleeve assembly (500) of this example comprises a flexible sleeve (510), a pair of anchor ends (530, 540), resilient member (550) extending between anchor ends (530, 540), and a sealing ring (522). Sleeve (510) of this example is substantially identical to sleeve (210) described above; and includes a proximal end (512) and a distal end (514). Anchor ends (530, 540) and resilient member (550) are substantially identical to anchor ends (230, 240) and resilient member (250), respectively, described above. Sealing ring (522) is substantially identical to sealing ring (322) described above. Like sleeve assembly (400) described above, sleeve assembly (500) of this example lacks seals (220, 320), though it should be understood that features like seals (220, 320) could be readily incorporated into sleeve assembly (500) if desired.

Unlike sleeve assemblies (200, 300, 400) described above, sleeve assembly (500) of the example shown in FIG. 6 includes an inflatable bladder (552) along part of the length of resilient member (550). Bladder (552) may be configured to receive air, liquid, gel, foam, etc. to transition from a deflated state to an inflated state. Bladder (552) may include a port enabling inflation/deflation of bladder (552) once sleeve assembly (552) is suitably positioned in the duodenum (140). In some versions, bladder (552) is filled with a foam material that is initially in a liquid state during filling; then transitions into a rigid or flexible member after a certain period. This may promote conformity with the unique curvature/configuration of the particular patient's duodenum (140), such that bladder (552) provides a customized fit on a per-patient basis. When sleeve assembly (500) is to be removed, a neutralizing agent may be injected into bladder (552) to re-liquefy the foam. In the inflated or otherwise formed state, bladder (552) defines a transverse cross-sectional area that is greater than the transverse cross-sectional area defined by resilient member (550). In the inflated or otherwise formed state, bladder (552) may thus provide a greater surface area for distributing the pressure from resilient member (550) on the mucosa of the duodenum (140), thereby softening the contact.

As shown in FIG. 6, a proximal portion of bladder (552) extends distally past sealing ring (522) in the present example, such that bladder (552) further cushions contact against the mucosa of the stomach (110). Alternatively, bladder (552) may distally terminate proximal to the proximal end (512) of sleeve (510). It should also be understood that the distal end of bladder (552) may terminate proximal to, at, or distal to distal anchor end (530). In some versions, bladder (552) comprises a component that is secured to sleeve (510) and/or resilient member (550). In some other versions, bladder (552) is defined as an integral sub-lumen of sleeve (510). For instance, bladder (552) may be formed as a lumen defined within the sidewall of sleeve (510). In some variations, bladder (552) serves as a substitute for resilient member (550). For instance, anchor ends (530, 540) may be secured to opposite ends of bladder (552), such that anchor ends (530, 540) and bladder (552) (in an inflated or otherwise formed state) cooperate to maintain the position of sleeve (510) within the duodenum (140). Other suitable forms that bladder (552) may take will be apparent to those of ordinary skill in the art in view of the teachings herein.

II. Exemplary Deployment of Duodenal Sleeve

FIGS. 7A-7G show an exemplary method of installing a sleeve assembly (600), which is an illustrative variation of sleeve assembly (200). While sleeve assembly (600) is used in this example, it should be understood that a substantially identical method may be used to install the various other sleeve assemblies (200, 300, 400, 500) described herein. Sleeve assembly (600) of this example comprises a flexible sleeve (610), a pair of anchor ends (630, 640), resilient member (650) extending between anchor ends (630, 640), and a proximal seal (620). Sleeve (610) of this example is substantially identical to sleeve (210) described above; and includes a proximal end (612) and a distal end (614). Anchor ends (630, 640) and resilient member (650) are substantially identical to anchor ends (230, 240) and resilient member (250), respectively, described above. Proximal seal (620) is substantially identical to the proximal-most seal (220) described above. Unlike sleeve assembly (200), however, sleeve assembly (600) of this example only has proximal seal (620), such that no additional seals are included. Resilient member (650) is secured to proximal seal (620) and is located exterior to sleeve (610). Resilient member (650) is not secured to any portion of sleeve (610) distal to proximal seal (620) in this example.

Figure 7A:
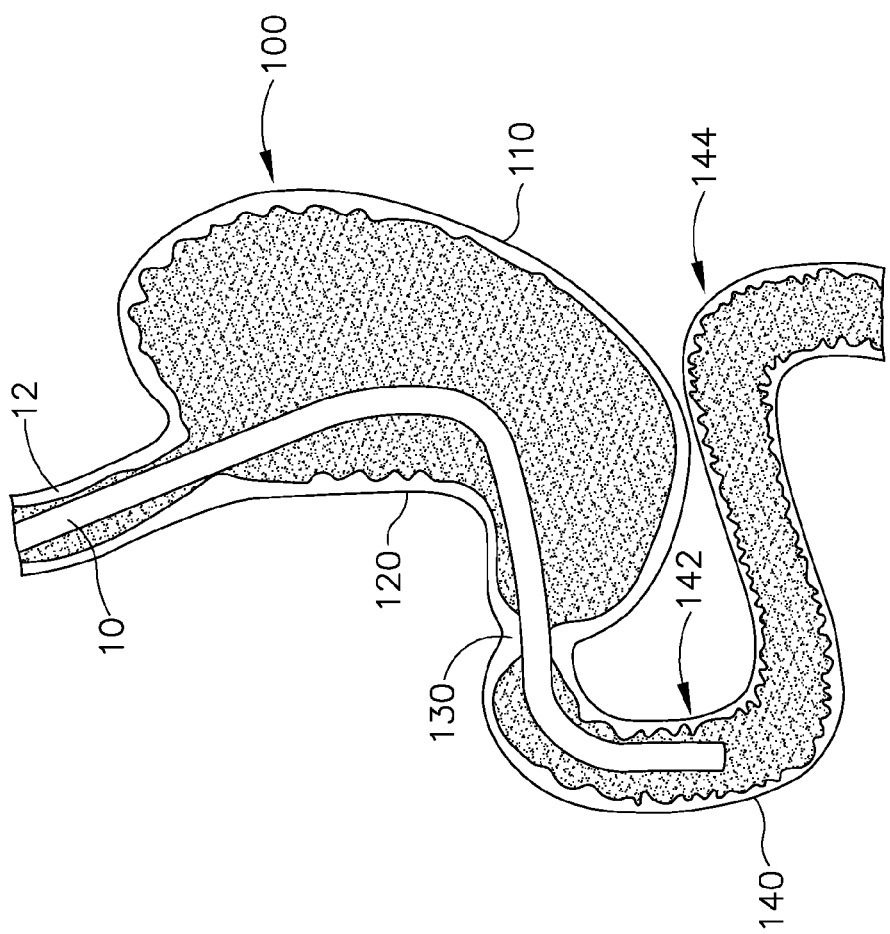
FIG. 7A depicts a side, elevation view of an endoscope inserted into the stomach and further through the pylorus into the duodenum.
Figure 7B:
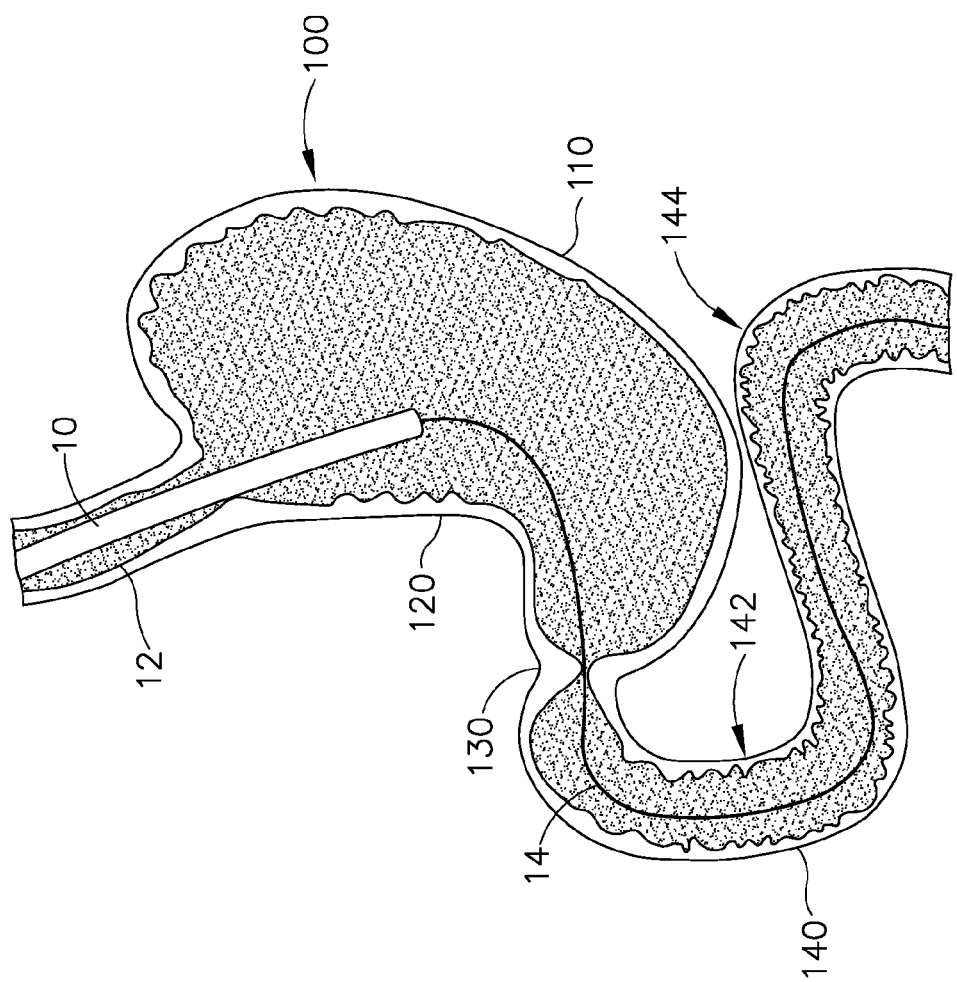
FIG. 7B depicts a side, elevation view of the scope of FIG. 7A with a guidewire advanced into the duodenum and the scope being retracted.
Figure 7C:
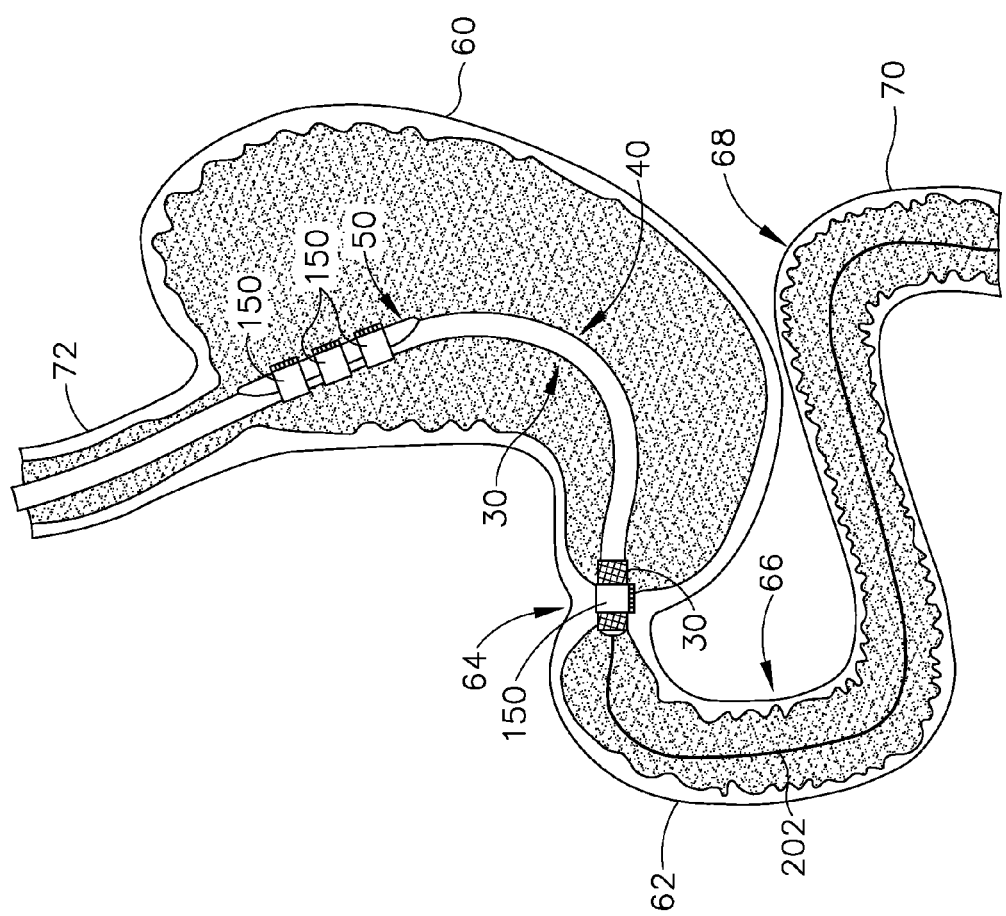
FIG. 7C depicts a side, elevation view of an insertion instrument being inserted into the duodenum through the pylorus along the guidewire of FIG. 7B.

In the present example, sleeve assembly (600) is installed using instruments inserted through the patient's mouth. In some other instances, sleeve assembly (600) may be installed through a surgically created opening or in some other fashion. FIG. 7A shows a conventional endoscope (10) inserted through the esophagus (12) into the stomach (100). Endoscope (10) has been further advanced through the pylorus (130), such that the operator is able to view the duodenum (140). It will be understood that, in addition to providing visualization of the duodenum (140) and portions of the stomach (100), endoscope (10) may be used to advance other instruments into the stomach (100) or the duodenum (140). FIG. 7B shows a conventional guidewire (14) inserted through the pylorus (130) and into the duodenum (140) via a working channel of endoscope (10), with endoscope (10) already being retracted through the esophagus (12) while guidewire (14) remains disposed in the duodenum (140). With guidewire (14) so positioned, and with endoscope (10) fully withdrawn from the esophagus (12), a deployment instrument (16) is advanced along guidewire (14) as shown in FIG. 7C. In some versions, deployment instrument (16) is configured and operable in accordance with at least some of the teachings of U.S. patent application Ser. No. 14/011,962, entitled "Endoscopic Transoral Duodenal Sleeve Applier," filed on Aug. 28, 2013, now U.S. Pat. Pub. No. 2015/0065938, Mar. 5, 2015, the disclosure of which is incorporated by reference herein.

Figure 7D:
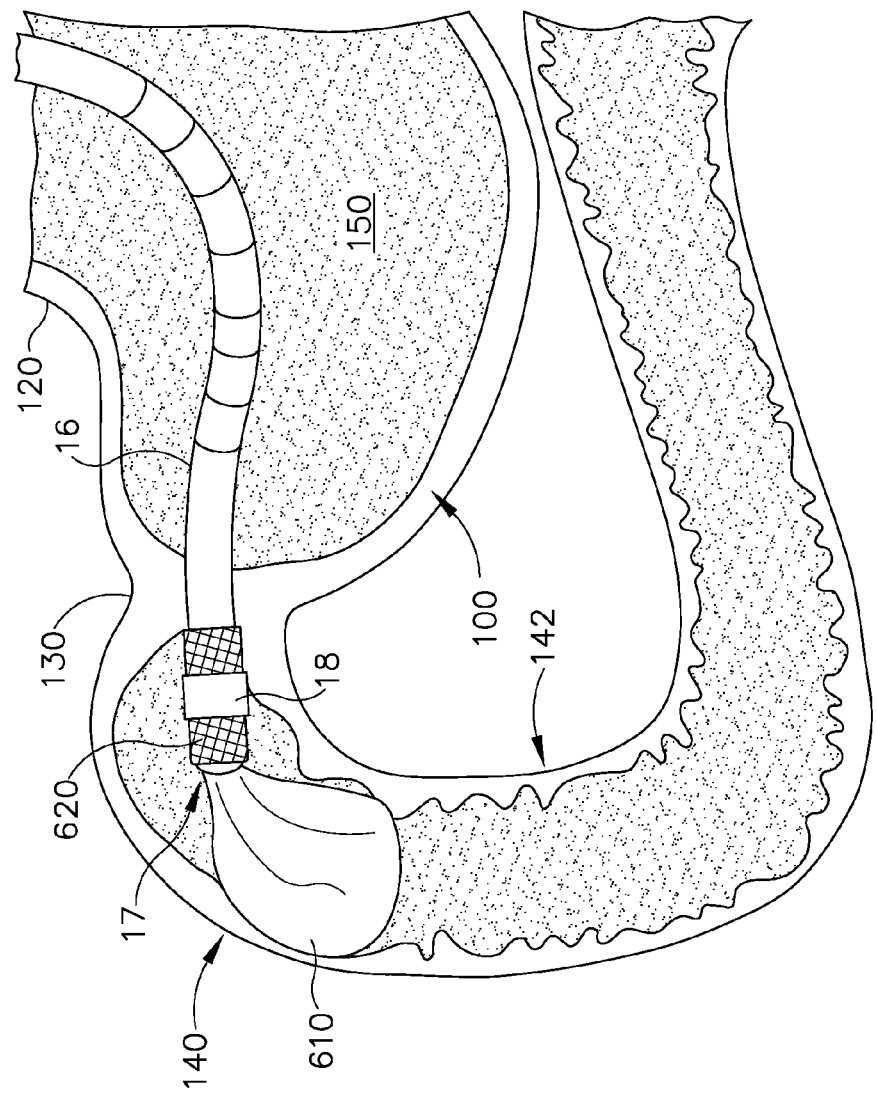
FIG. 7D depicts a side, elevation view of the insertion instrument of FIG. 7C with a sleeve assembly being advanced into the duodenum.

Deployment instrument (16) carries sleeve assembly (600) in the present example. As shown in FIGS. 7C-7D, deployment instrument (16) is advanced such that the distal end (17) of deployment instrument (16) passes through the pylorus (130) and into the duodenum (140). A retaining member (18) secures proximal seal (620) to the distal end (17) of deployment instrument (16) during this insertion stage; while sleeve (610), anchor ends (630, 640), and resilient member (650) are held in the interior of deployment instrument (16). As shown in FIG. 7D, deployment instrument (16) begins to deploy sleeve (610) once proximal seal (620) is positioned distal to the pylorus (130). In particular, sleeve (610) is initially held in the interior of deployment instrument (16) in an inverted configuration, and a fluid (e.g., air, saline, etc.) is then communicated through the interior of deployment instrument (16) to make sleeve (610) unfurl distally from the distal end (17) of deployment instrument (16).

Figure 7E:
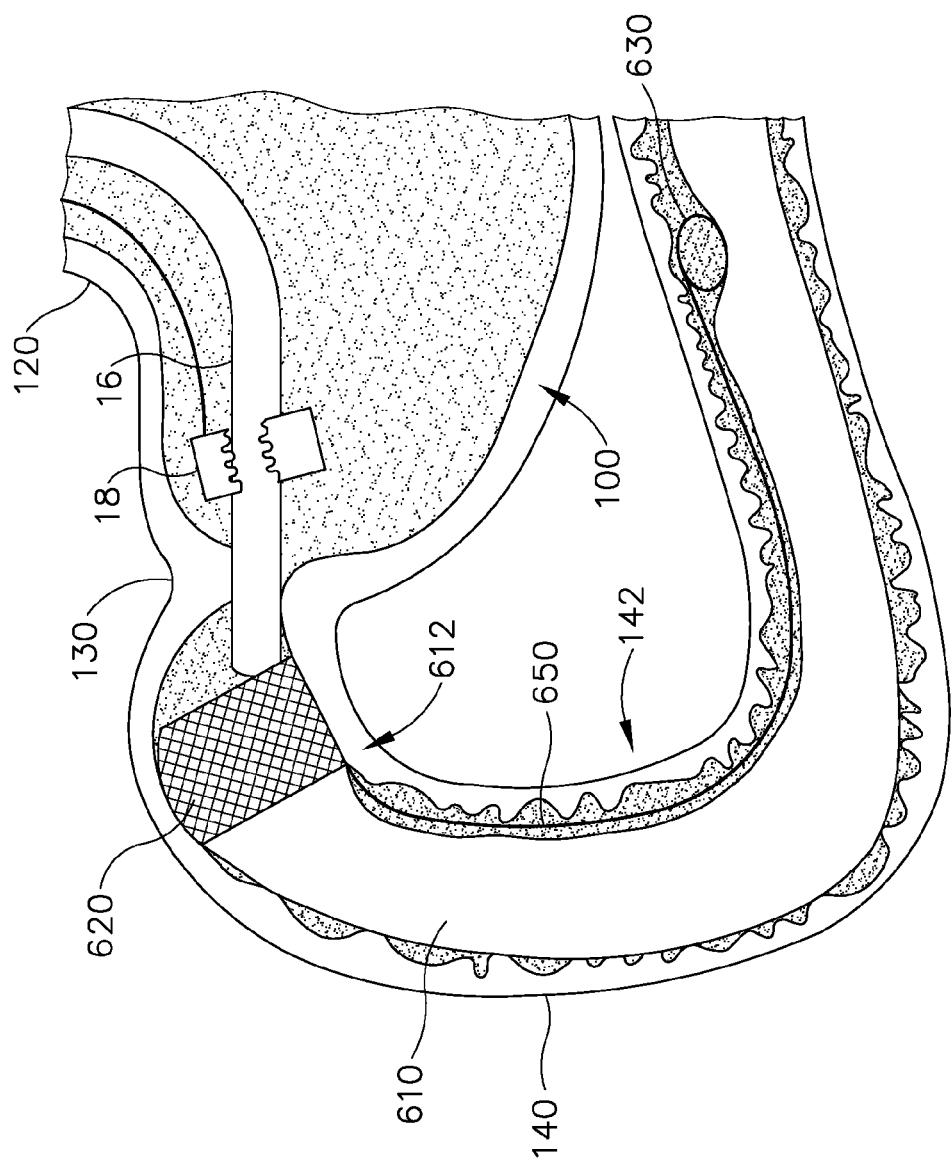
FIG. 7E depicts a side, elevation view of the insertion instrument of FIG. 7C with the sleeve fully deployed and an anchor being deployed.
Figure 7F:
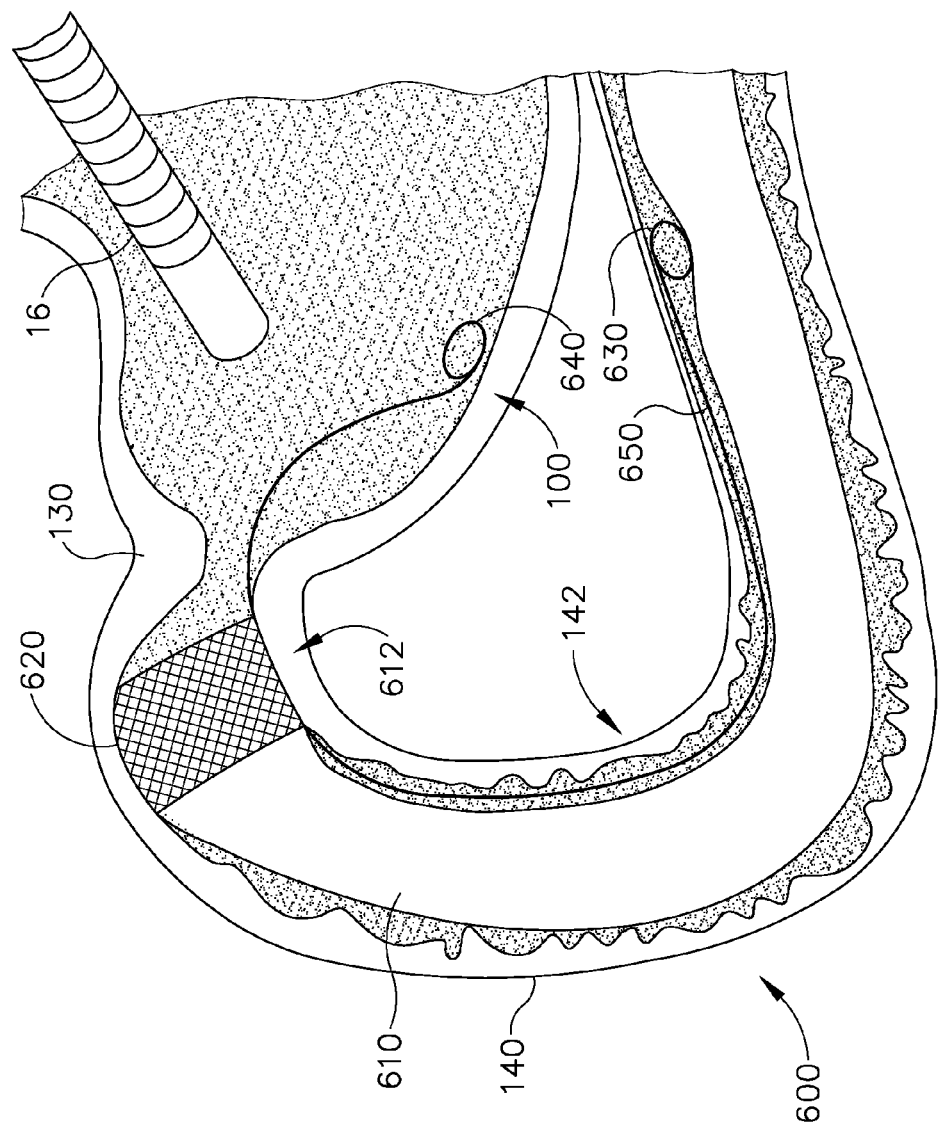
FIG. 7F depicts a side, elevation view of the sleeve assembly of FIG. 7E fully deployed and the insertion instrument being removed.

Once sleeve (610) has been deployed from deployment instrument (16), retaining member (18) is actuated to release proximal seal (620) from the distal end (17) of deployment instrument (16) as shown in FIG. 7E. This allows proximal seal (620) to resiliently expand outwardly into engagement with the mucosa of the duodenum (140), between the ampulla of Vater (142) and the pylorus (130), thereby sealing sleeve (610) against the mucosa. As also shown in FIG. 7E, resilient member (650) and anchor end (630) are also deployed such that anchor end (630) is positioned near the duodenojejunal flexure (144). It should be understood that resilient member (650) deforms to assume a substantially straight configuration while being advanced through or along deployment instrument (16); then resiliently assumes a bent configuration after passing from distal end (17) of deployment instrument (160). After releasing proximal seal (620) and advancing anchor end (630) into position, deployment instrument (16) is then retracted proximally, deploying anchor end (640) such that anchor end (640) eventually engages the mucosa of the stomach (100) as shown in FIG. 7F. Anchor ends (630, 640) and resilient member (650) cooperate to substantially anchor sleeve (610) in the duodenum (140). Deployment instrument (16) is then fully withdrawn via the esophagus (12), leaving sleeve assembly (600) in the deployed state as shown in FIG. 7G.

Figure 7G:
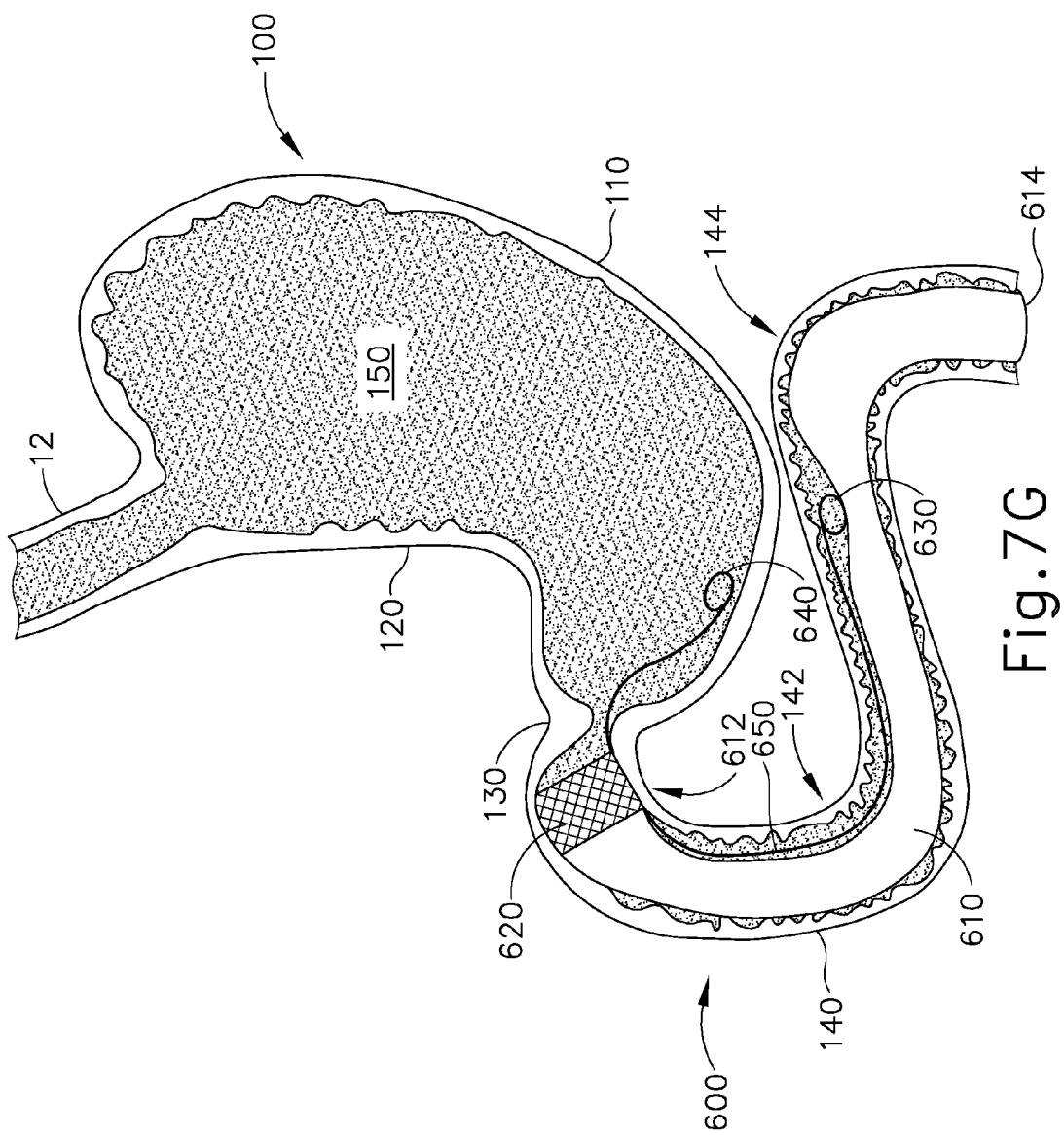
FIG. 7G depicts a side, elevation view of the sleeve assembly of FIG. 7E fully deployed and the insertion instrument fully removed.

As shown in FIG. 7G, the sleeve (610) and resilient member (650) are sized and positioned such that distal end (614) of sleeve (610) is located distal to distal anchor end (630). In some instances (e.g., as shown in FIG. 7G) distal end (614) is distal to the duodenojejunal flexure (144) while distal anchor end (630) is proximal to the duodenojejunal flexure (144). In some other instances, distal end (614) is located at the duodenojejunal flexure (144) or just proximal to the duodenojejunal flexure (144); while distal anchor end (630) is still proximal to distal end (614). Other suitable locations for distal end (614) upon deployment of sleeve assembly (600) will be apparent to those of ordinary skill in the art in view of the teachings herein.

Of course, there are numerous other suitable ways in which a sleeve assembly (200, 300, 400, 500, 600) may be deployed. By way of example only, sleeve assembly (200, 300, 400, 500, 600) may be deployed in accordance with at least some of the teachings of U.S. patent application Ser. No. 14/011, 962, entitled "Endoscopic Transoral Duodenal Sleeve Applier," filed on Aug. 28, 2013, now U.S. Pat. Pub. No. 2015/0065938, published Mar. 5, 2015, the disclosure of which is incorporated by reference herein. It should also be understood that sleeve (210, 310, 410, 510, 610) may be deployed first (e.g., using a first deployment instrument); then the anchor assembly formed by corresponding anchors (230, 240, 330, 340, 430, 440, 530, 540, 630, 640) and resilient member (250, 350, 450, 550, 650) may be deployed (e.g., using a second deployment instrument) after sleeve (210, 310, 410, 510, 610) has been deployed. Still other suitable ways in which sleeve assembly (200, 300, 400, 500, 600) may be deployed will be apparent to those of ordinary skill in the art in view of the teachings herein.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application. Of course, the devices described herein may alternatively be disposed of after a single use, and need not be reconditioned or reused.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
    (a) a flexible, non-permeable sleeve configured to fit in a duodenum, wherein the sleeve includes a distal end and a proximal end, wherein the sleeve is configured to define a first lumen;
    (b) a seal positioned at the proximal end of the sleeve, wherein the seal is configured to maintain patency of the first lumen at the proximal end of the sleeve, wherein the seal is further configured to seal the proximal end of the sleeve against an anatomical structure associated with the duodenum;
    (c) an anchor assembly, wherein the anchor assembly comprises:
        (i) a distal anchor end,
        (ii) a proximal anchor end, and
        (iii) a resilient member positioned between the distal anchor end and the proximal anchor end, wherein at least a portion of the resilient member extends along at least a portion of the length of the sleeve, wherein the resilient member is configured to bias the anchor ends generally toward each other.

2. The apparatus of claim 1, wherein the first anchor end and the second anchor end each have atraumatic shapes.

3. The apparatus of claim 2, wherein the first anchor end and the second anchor end each define a loop shape.

4. The apparatus of claim 1, wherein the resilient member is biased to assume a bent configuration.

5. The apparatus of claim 1, wherein the resilient member is secured to the seal.

6. The apparatus of claim 5, wherein the resilient member is not directly secured to a portion of the sleeve distal to the seal.

7. The apparatus of claim 1, wherein at least one of the anchor ends includes an integral bladder.

8. The apparatus of claim 1, wherein the seal comprises a stent.

9. The apparatus of claim 8, wherein the stent is resiliently biased to define a circumference larger than a pylorus.

10. The apparatus of claim 1, wherein the distal anchor end is positioned within the sleeve.

11. The apparatus of claim 1, wherein the proximal anchor end is positioned proximal to the sleeve.

12. The apparatus of claim 1, wherein the proximal anchor end is positioned proximal to the seal.

13. The apparatus of claim 1, further comprising a fillable member extending along at least part of the length of the resilient member.

14. The apparatus of claim 13, wherein the fillable member includes a foam material.

15. The apparatus of claim 13, wherein the fillable member comprises a second lumen defined in a sidewall of the sleeve.

16. The apparatus of claim 1, wherein the resilient member is secured to the sleeve.

17. An apparatus comprising:
(a) a resilient member comprising a wire positionable along a curvature of a duodenum, wherein the resilient member is moveable between a first configuration and a second configuration, wherein the member has a straight shape in the first configuration, wherein the resilient member has a bent shape in the second configuration, wherein the resilient member is resiliently biased to assume the second configuration;
(b) a first anchor end positioned at a distal end of the resilient member;
(c) a second anchor end positioned at a proximal end of the resilient member;
(d) a flexible sleeve extending along at least part of the resilient member, wherein the flexible sleeve and the resilient member are configured to fit within a duodenum; and
(e) a sealing member, wherein the sealing member is configured to seal the flexible sleeve against an anatomical structure associated with the duodenum.

18. A method of installing a duodenal sleeve using an insertion instrument in a duodenum and stomach of a patient, wherein the duodenal sleeve comprises a resilient member, a flexible sleeve, a first anchor end, and a second anchor end, wherein the flexible sleeve has a distal end and a proximal end, the method comprising:
(a) advancing a distal end of the insertion instrument into the duodenum;
(b) advancing the flexible sleeve into the duodenum;
(c) sealing the proximal end of the flexible sleeve against an anatomical structure associated with the duodenum, wherein the anatomical structure associated with the duodenum comprises mucosa of the duodenum, mucosa of the stomach, or the pylorus;
(d) positioning the first anchor end in the duodenum;
(e) positioning the second anchor end in the stomach; and
(f) releasing the resilient member from the insertion instrument, wherein the released resilient member urges the first and second anchor ends generally toward each other to substantially secure the sleeve in the duodenum.

* * * * *